United States Patent
Masumoto et al.

(10) Patent No.: US 8,497,862 B2
(45) Date of Patent: Jul. 30, 2013

(54) METHOD AND APPARATUS FOR PROCESSING THREE DIMENSIONAL IMAGES, AND RECORDING MEDIUM HAVING A PROGRAM FOR PROCESSING THREE DIMENSIONAL IMAGES RECORDED THEREIN

(75) Inventors: Jun Masumoto, Ichikawa (JP); Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 1030 days.

(21) Appl. No.: 12/100,942

(22) Filed: Apr. 10, 2008

(65) Prior Publication Data

US 2009/0096787 A1   Apr. 16, 2009

(30) Foreign Application Priority Data

Apr. 12, 2007   (JP) .................. 2007-105195

(51) Int. Cl.
*G06T 17/00*   (2006.01)
(52) U.S. Cl.
USPC ........................................... 345/424
(58) Field of Classification Search
USPC ........................................... 345/424
See application file for complete search history.

(56) References Cited

U.S. PATENT DOCUMENTS

| | | | |
|---|---|---|---|
| 6,480,732 B1 | 11/2002 | Tanaka et al. | |
| 6,674,430 B1 * | 1/2004 | Kaufman et al. | 345/419 |
| 6,807,247 B2 * | 10/2004 | Krishnan et al. | 378/4 |
| 7,110,616 B2 * | 9/2006 | Ditt et al. | 382/284 |
| 7,616,799 B2 * | 11/2009 | Ramamurthy et al. | 382/131 |
| 7,711,162 B2 * | 5/2010 | Li | 382/128 |
| 2006/0229513 A1 | 10/2006 | Wakai | |
| 2006/0239524 A1 | 10/2006 | Desh et al. | |
| 2006/0256111 A1 * | 11/2006 | Chihoub et al. | 345/424 |
| 2007/0002046 A1 * | 1/2007 | Tanacs et al. | 345/424 |
| 2007/0078325 A1 | 4/2007 | Fuimaono et al. | |
| 2009/0074264 A1 | 3/2009 | Pekar et al. | |

FOREIGN PATENT DOCUMENTS

| | | |
|---|---|---|
| JP | 2001-14446 A | 1/2001 |
| JP | 2006-288495 A | 10/2006 |
| WO | WO 2006/054194 A2 | 5/2006 |

OTHER PUBLICATIONS

Annex to the European Search Report on European Patent Application No. EP 08 00 7213, dated Sep. 14, 2012.
EP Search Report issued in corresponding EP Application No. 08007213.5-1522 / 1988511 on Sep. 25, 2012.

(Continued)

*Primary Examiner* — Edward Martello
(74) *Attorney, Agent, or Firm* — Birch, Stewart, Kolasch & Birch, LLP

(57) ABSTRACT

A pseudo three dimensional image is generated, based on an aspect image and a mapping image generated from an original three dimensional image, using a volume rendering method. A mapping image that represents the functions of a subject is generated using first voxel data that constitute an original three dimensional medical image of the subject. An aspect image is generated using second voxel data that constitute an original three dimensional medical image of the subject. A position matching means causes positions within a heart represented by the mapping image to correspond to positions within a heart represented by the aspect image. An image generating means executes volume rendering based on degrees of opacity within the mapping image, to generate the pseudo three dimensional image.

14 Claims, 5 Drawing Sheets

OTHER PUBLICATIONS

Gaemperli et al., "Validation of a New Cardiac Image Fusion Software For Three-Dimensional Integration of Myocardial Perfusion SPECT and Stand-Alone 64-Slice CT Angiography", European Journal of Nuclear Medicine and Molecular Imaging, Springer, Berlin, DE, vol. 34, No. 7, Jan. 24, 2007, pp. 1097-1106, XP-19514023.

Zhang, et al., "Real-Time Dynamic Display of Registered 4D Cardiac MR and Ultrasound Images Using a GPU", Medical Imaging 2007: Visualization and Image-Guided Procedures, Feb. 18, 2007, San Diego, CA, vol. 6509, pp. 1-11, XP55037950.

Cai et al., "Data Intermixing and Multi-Volume Rendering", Computer Graphics Forum, vol. 18, No. 3, Sep. 7, 1999, pp. C359-C368, C425, XP001034487.

Ferre, et al., "A Framework for Fusion Methods and Rendering Techniques of Multimodal Volume Data", Computer Animation and Virtual Worlds, vol. 15, Jan. 1, 2004, pp. 63-77, XP007905457.

\* cited by examiner

PSEUDO THREE DIMENSIONAL IMAGE

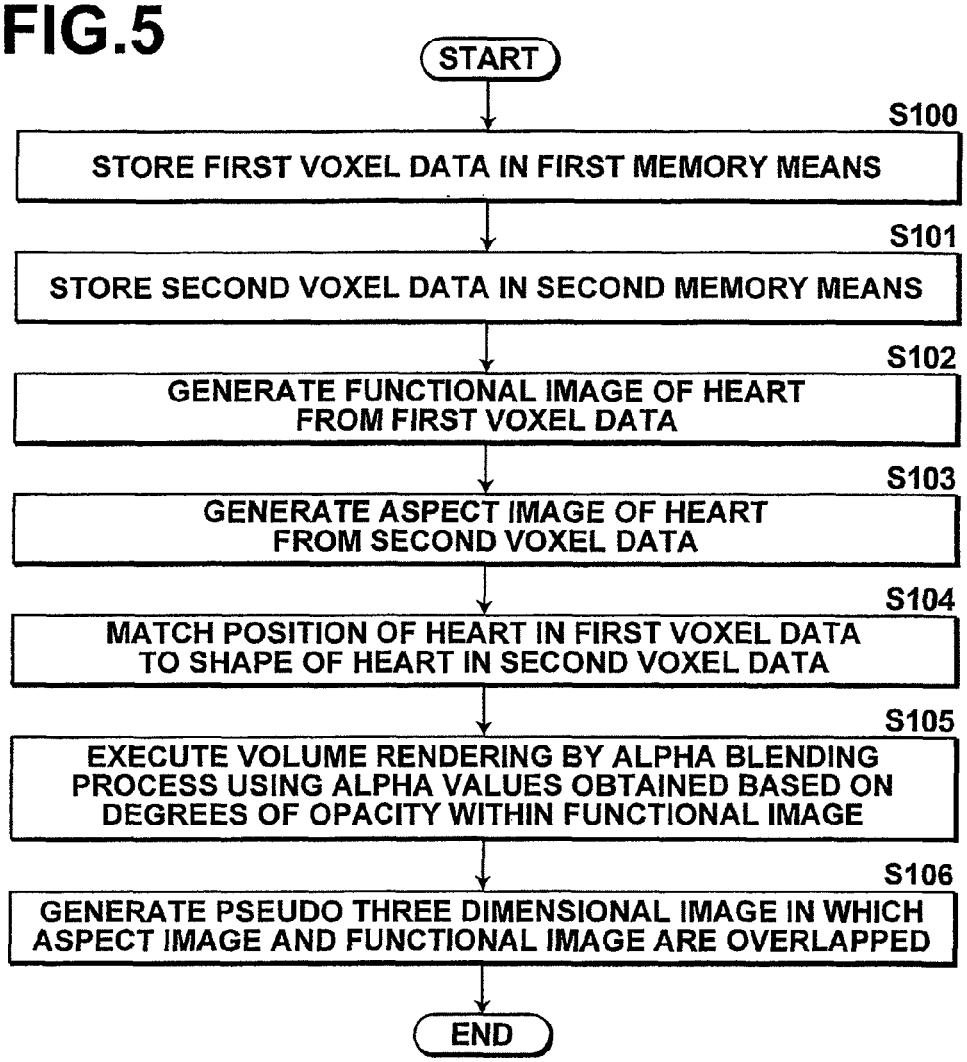

METHOD AND APPARATUS FOR PROCESSING THREE DIMENSIONAL IMAGES, AND RECORDING MEDIUM HAVING A PROGRAM FOR PROCESSING THREE DIMENSIONAL IMAGES RECORDED THEREIN

BACKGROUND OF THE INVENTION

1. Field of the Invention

The present invention relates to volume rendering of medical images. More specifically, the present invention relates to an image processing method and an image processing apparatus that execute volume rendering, using aspect images that represent the shapes of subjects and mapping images that represent functions of the subjects, such as the thicknesses and the properties thereof. The present invention also relates to a recording medium having an image processing program recorded therein.

2. Description of the Related Art

Obtainment of detailed medical tomographic images has become possible, due to developments in CT apparatuses, MRI apparatuses, and ultrasound (echo) diagnostic apparatuses. Accompanying these developments, the number of images which are obtained during a single examination has also become large. Accordingly, conventional diagnostic methods, in which obtained tomographic images are examined one by one, takes an enormous amount of time. In addition, sufficient experience is required to conceptualize the three dimensional structure of a subject based on tomographic images. Therefore, differences in the accuracy of image diagnosis have occurred due to the difference in the experience of radiologists.

Therefore, three dimensional computer graphics technology has been applied to perform image processes that generate pseudo three dimensional images, in which subjects are visualized three dimensionally on a two dimensional plane, from a plurality of two dimensional tomographic images.

The volume rendering method is a known technique for generating pseudo three dimensional images. In the volume rendering method, opacity values are set for each pixel (voxel data) that constitutes an original three dimensional image data set. The opacity values and the brightness values of the voxels are sampled at each search point along lines of sight and added, to obtain output pixel values of a projected image, to generate a semitransparent pseudo three dimensional image.

Meanwhile, functional images that represent the thicknesses, functions, and the like of each portion of imaged subjects, which are directly obtained by myocardial scintigraphy (SPECT) or obtained indirectly from analysis results of MRI apparatuses and the like, are also known.

Japanese Unexamined Patent Publication No. 2006-288495 discloses an apparatus that extracts portions of interest from functional images. Then, the apparatus generates volume data sets, which are the functional images synthesized with aspect images, obtained by X ray CT apparatuses, MRI apparatuses, ultrasound diagnostic apparatuses or the like, that represent the shapes of subjects. Finally, the apparatus administers a volume rendering process on the synthesized volume data.

However, the following problem exists when an aspect image of a portion of a subject represented by three dimensional image data and a functional image is synthesized and volume rendering is executed. The shape of the aspect image, which represents the shape of the portion of the subject, cannot be maintained, and a pseudo three dimensional image, which is dependent on the shape of the functional image, is generated.

SUMMARY OF THE INVENTION

The present invention has been developed in view of the foregoing circumstances. It is an object of the present invention to provide a three dimensional image processing method, a three dimensional image processing apparatus, and a three dimensional image processing program, which are capable of mapping information of functional images and the like, which are present at positions corresponding to positions within aspect images.

A three dimensional image processing apparatus of the present invention comprises:

mapping image generating means, for generating a mapping image that represents a portion of a subject, by employing a first voxel data set, which is a voxel data set of a three dimensional image that represents the subject with at least a degree of opacity designated to each pixel thereof;

aspect image generating means, for generating an aspect image that represents the aspect of a target which includes at least a portion of the subject from a second voxel data set of the three dimensional image that represents the subject; and image generating means, for generating a pseudo three dimensional image, by matching each position within the mapping image and the aspect image and executing volume rendering based on the degrees of opacity within the mapping image.

A three dimensional image processing method of the present invention comprises:

a mapping image generating step, for generating a mapping image that represents a portion of a subject, by employing a first voxel data set, which is a voxel data set of a three dimensional image that represents the subject with at least a degree of opacity designated to each pixel thereof;

an aspect image generating step, for generating an aspect image that represents the aspect of a target which includes at least a portion of the subject from a second voxel data set of the three dimensional image that represents the subject; and an image generating step, for generating a pseudo three dimensional image, by matching each position within the mapping image and the aspect image and executing volume rendering based on the degrees of opacity within the mapping image.

A recording medium of the present invention has stored therein a three dimensional image processing program that causes a computer to function as:

mapping image generating means, for generating a mapping image that represents a portion of a subject, by employing a first voxel data set, which is a voxel data set of a three dimensional image that represents the subject with at least a degree of opacity designated to each pixel thereof;

aspect image generating means, for generating an aspect image that represents the aspect of a target which includes at least a portion of the subject from a second voxel data set of the three dimensional image that represents the subject; and image generating means, for generating a pseudo three dimensional image, by matching each position within the mapping image and the aspect image and executing volume rendering based on the degrees of opacity within the mapping image.

The "mapping image" refers to an image that represents the properties of a portion of a subject. The "mapping image" is used when imparting a variety of effects, such as patterns and texture, onto the surface of an object in the field of three dimensional computer graphics. A functional image is a specific example of the "mapping image".

The "functional image" refers to an image that enables visual recognition of the function of each position within a portion of the subject.

"Volume rendering" refers to a process in which degrees of opacity and brightness values or the like, which are set for each pixel (voxel data) that constitutes a three dimensional medical image, are sampled for each search point along lines of sight, then adding the values to generate a projection image. A specific example of a volume rendering method is the ray casting technique.

"Brightness values" refer to values that represent brightness, calculated for each search point. The values are calculated based on the pixel values of pixels that constitute an original three dimensional image, color data corresponding to the pixel values of pixels that constitute the original three dimensional image, luminosity, which is determined by the image gradient and the relationships with a light source at each search point, and the like.

The "ray casting technique" is a technique in which: a virtual ray of light is irradiated onto an object from a projection plane; and a three dimensional image is generated from virtual light reflected from the interior of the object, based on degrees of opacity, brightness values and the like corresponding to voxel values. Thereby, a projection image is generated, in which the three dimensional structure of the interior of the object can be viewed.

The three dimensional image processing apparatus, the three dimensional image processing method, and the three dimensional image processing program stored in the recording medium of the present invention execute volume rendering by matching each position within the mapping image and the aspect image, then executing volume rendering based on the degrees of opacity within the mapping image. Therefore, data within the mapping image at positions corresponding to positions within the aspect image are mapped, and generation of pseudo three dimensional images which are faithful to the shapes of aspect images, and not dependent on the shapes of mapping images, becomes possible.

BEST MODE FOR CARRYING OUT THE INVENTION

Figure 1:
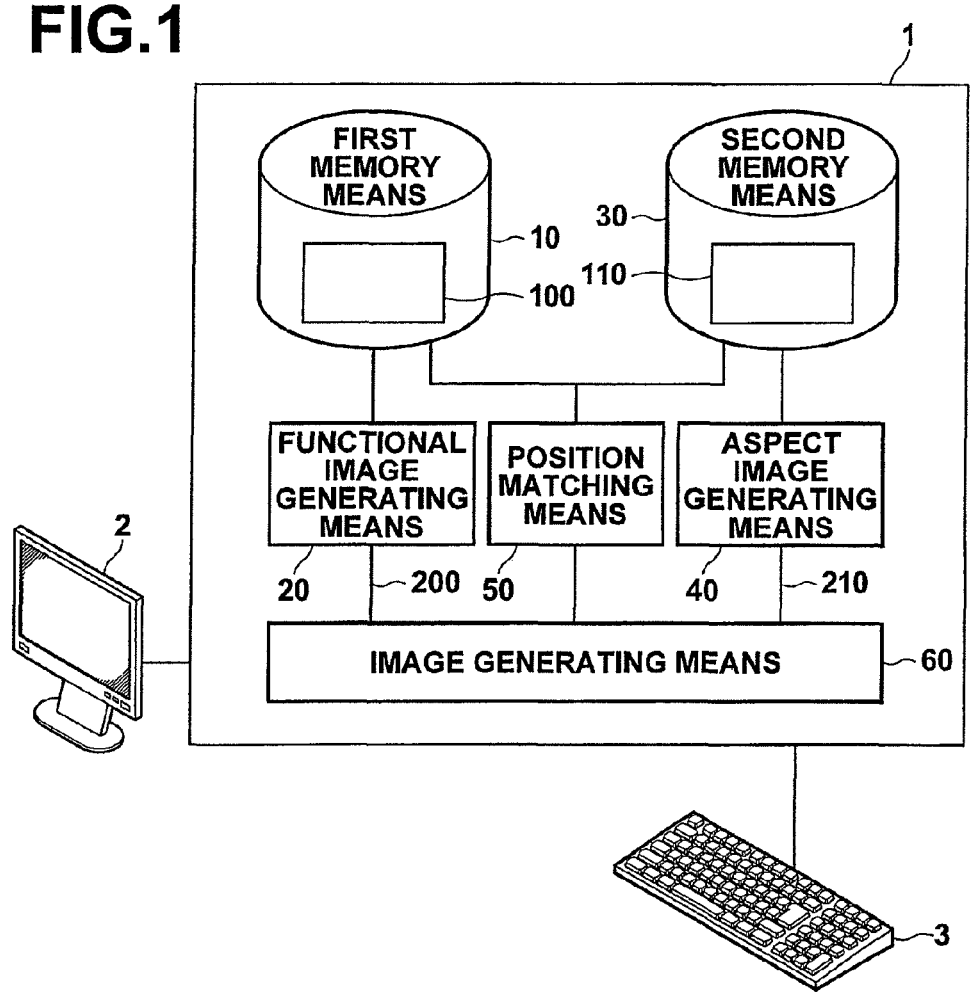
FIG. 1 a schematic diagram that illustrates the construction of a pseudo three dimensional image generating apparatus of the present invention FIG. 2 a diagram for explaining conversion in the ray casting technique FIG. 3 a diagram for explaining conversion from an aspect image coordinate system to a mapping image coordinate system FIG. 4 a first example of an image in which the aspect image and a functional image are overlapped FIG. 5 a flow chart of the processes of the present invention for generating a pseudo three dimensional image

Hereinafter, an embodiment of the three dimensional image processing apparatus of the present invention will be described with reference to the attached drawings. FIG. 1 is a schematic diagram that illustrates the structure of a three dimensional image processing apparatus 1 of the present invention. Note that the configuration of the three dimensional image processing apparatus 1 illustrated in FIG. 1 is realized by executing a three dimensional image processing program, which is read out from an auxiliary memory device, on a computer. At this time, the three dimensional image processing program may be distributed being recorded in recording media such as CD-ROM's, or via a network such as the Internet, and installed in the computer.

The three dimensional image processing apparatus 1 of the present invention is constituted by: a first memory means 10, for storing first voxel data sets 100 that constitute three dimensional medical images obtained by imaging subjects; a functional image generating means 20, for generating functional images 200 that represent the functions of each position of the heart, using the first voxel data sets 100; a second memory means 30, for storing second voxel data sets 110 that constitute the three dimensional medical images obtained by imaging the subjects; an aspect image generating means 40, for generating aspect images 210 that illustrate the aspect of the heart, using voxel data from among the second voxel data sets 110 that represent the region of the heart, which is a portion of the images that represent the subjects; a position matching means 50, for matching the positions of the first voxel data sets 100 and the second voxel data sets 110; an image generating means 60, for executing volume rendering using the aspect images 210 and the functional images 200; a display means 2, for displaying the pseudo three dimensional images generated by the image generating means 60; and an input means 3, for enabling data input by an operator.

The first voxel data sets 100 and the second voxel data sets 110 are original three dimensional images obtained by imaging using CT (Computed Tomography) apparatuses, MRI (Magnetic Resonance Imaging) apparatuses and the like. The first voxel data sets are used to generate the functional images 200, and the second voxel data sets 110 are used to generated the aspect images 210.

The first memory means 10 and the second memory means 30 are high capacity memory devices, such as hard disks, image servers, or the like. The first voxel data sets 100 and the second voxel data sets 110, which are obtained by imaging subjects using CT apparatuses, MRI apparatuses and the like, are recorded in the first memory means 10 and the second memory means 30.

A mapping image is an image that represents the properties of a portion of a subject. The "mapping image" is used when imparting a variety of effects, such as patterns and texture, onto the surface of an object during volume rendering or the like in the field of three dimensional computer graphics. A functional image is a specific example of the "mapping image". The functional images 200 will be described hereinafter.

The functional images 200 represent distributions of evaluation values (with colors or numerical values) for heart functions, which are evaluated according to the movement of the heart, the inner diameters of the ventricles, the thickness of the cardiac muscle, etc. Specific examples of the functional images 200 include: a ventricular diameter image that represents the diameter of a ventricle in a given phase; a telediastolic ventricular diameter image that represents the diameter of a ventricle in the diastolic phase; a systolic ventricular diameter image that represents the diameter of a ventricle in the systolic phase; a local ejection fraction image that represents the ejection fraction for each of a plurality of sectioned regions; a wall thickness image that represents the thickness of the cardiac muscle in a given phase; a telediastolic wall thickness image that represents the thickness of the cardiac muscle in the diastolic phase; a systolic wall thickness image that represents the thickness of the cardiac muscle in the systolic phase; a wall thickness variation image that represents the difference between the thickness of the cardiac muscle in the diastolic phase and the thickness of the cardiac muscle in the systolic phase; a wall thickness increase rate that represents a value calculated according to a formula (B−A)/A, when the thickness of the cardiac muscle during the diastolic phase is designated as A, and the thickness of the cardiac muscle during the systolic phase is designated as B; a quantity of wall action image that represents the difference between the ventricular diameter during the diastolic phase and the ventricular diameter during the systolic phase; and a myocardial scintigraphy image.

The functional images 200 that represent myocardial scintigraphy are images that represent data obtained by myocardial scintigraphy. In myocardial scintigraphy, a chemical that accumulates in the heart is injected into a subject's arm, and the distribution of the chemical is externally measured, to obtain the data. The state of blood flow within the heart, the metabolism of the cardiac system, the actions of nerves, etc. can be represented, by changing the chemical which is injected.

In the case that evaluations of cardiac action are represented by the functional images 200, images of a heart in action are obtained during a plurality of phases, evaluation values of heart functions are obtained from the differences among the images, and the functional images 200 are generated from the obtained evaluation values. In the case that images are obtained during a plurality of phases in this manner, it is desirable for the functional images 200 to be generated from images obtained by MRI apparatuses, which do not irradiate subjects.

Meanwhile, the aspect images 210 are images that represent the aspect of the heart. It is preferable for the aspect images 210 to be generated from original three dimensional images obtained by CT apparatuses, in which the structures of each organ are clearly represented.

It is preferable for the aspect images 210 to include targets that include portions of the subjects of the functional images 200.

It is preferable for voxel data generated from tomographic images obtained by CT apparatuses, MRI apparatuses and the like at fine pitches (intervals of 1 mm to 3 mm, for example) to be employed for the second voxel data sets, which are employed to generate the aspect images 210. The voxel data generated from the tomographic images which are obtained at fine pitches are employed such that the aspect images 210 can represent the aspects of the subjects in detail. On the other hand, when it is necessary to obtain images of the heart in action during a plurality of phases to generate the functional images 200, there are cases in which images of the heart cannot be obtained at a plurality of phases if imaging is performed at fine pitches. Therefore, it is common for voxel data generated from tomographic images obtained by MRI apparatuses and the like at wider pitches (intervals of 5 mm to 10 mm, for example) to be employed as the first voxel data sets.

The position matching means 50 matches the positions of the hearts represented by the first voxel data sets 100 and the hearts represented by the second voxel data sets 110. For example, assume a case in which a first voxel data set 100 is an image of a heart obtained by an MRI apparatus, and a second voxel data set 110 is an image of the heart obtained by a CT apparatus. In this case, it is difficult for imaging to be performed such that the subject is positioned exactly the same in both images, even if images of the same subject are obtained. Therefore, positions are matched between the shape of the heart represented by the first voxel data set 100 and the shape of the heart represented by the second voxel data set 110, in order to project the aspects of blood vessels, which are present in the periphery of the heart, onto the position of the corresponding heart in a functional image 200.

The position matching can be performed by employing various techniques called registration. Here, a specific example will be considered, in which a point $x_A$ within an image A represented by the first voxel data set 100 is converted to a point $x_B$ within an image B represented by the second voxel data set 110.

If a converting function is designated as T, T can be expressed by the following formula:

$$T: x_A \to x_R$$

$$T(x_A) = x_R \quad (1)$$

If the shape of the heart is considered to be a rigid body, converting functions are represented by movement ($t_x$, $t_y$, and $t_z$) in the X axis direction, the Y axis direction, and the Z axis direction within a three dimensional space, as well as rotation ($\alpha$, $\beta$, and $\gamma$) about each axis. The converting functions are illustrated by the formula below:

$$T = \begin{pmatrix} \cos\beta\cos\gamma & \cos\alpha\cos\gamma + \sin\alpha\sin\beta\cos\gamma & \sin\alpha\sin\gamma - \cos\alpha\sin\beta\cos\gamma & t_x \\ -\cos\beta\sin\gamma & \cos\alpha\cos\gamma - \sin\alpha\sin\beta\cos\gamma & \sin\alpha\cos\gamma + \cos\alpha\sin\beta\cos\gamma & t_y \\ \sin\beta & -\sin\alpha\cos\beta & \cos\alpha\cos\beta & t_z \\ 0 & 0 & 0 & 1 \end{pmatrix} \quad (2)$$

Because the shape of the heart varies, the heart may be considered to be a non rigid body. In this case, the degree of freedom increases, and therefore, T is expressed as a complex function that includes polynomials, spline functions, and the like.

Specifically, the converting functions may be derived by detecting several (for example, three) anatomical points which are features of the heart, then deriving the converting functions therefrom. Alternatively, the outline of an image may be determined, and the converting functions may be derived by repeating fitting processes such that distances between point sequences corresponding to the surface of another image becomes minimal. As a further alternative, the degrees of similarity among the pixel values of all voxels within images may be examined, and the images may be overlapped. If all of the pixel values within the images are employed in this manner, noise components in the pixels cancel each other out, and comparatively stable results can be obtained (for details of this process, refer to pp. 60-65, Journal of the Japanese Radiological Society, Vol. 53, No. 1, January 2003 and the like).

Positional matching may be performed by employing any of the registration techniques described above.

When the coordinate converting functions are defined, the second voxel data set 110 is an independent data set. Therefore, the visualization conditions of the second voxel data set 110 are maintained and the first voxel data set 100 is changed, to enable mapping of different data with respect to the same shape.

The image generating means 60 causes each position within an aspect image 210 and a functional image 200 to correspond to each other, based on the correspondent data between the first voxel data set 100 and the second voxel data set 110, calculated by the position matching means 50. Then, the image generating means 60 executes volume rendering using the brightness values (color data and the like, which are assigned to each pixel value of the voxel data sets) within each of the aspect image and the functional image, based on the degree of opacity corresponding to each position of the functional image, to generate a pseudo three dimensional image.

The ray casting technique may be used as a specific volume rendering method, for example. The ray casting technique generates images that reflect data regarding interiors as well, by calculating concentration/density data along lines of sight that extend from the images, with respect to volume data, which are defined by concentrations and densities.

An aspect image 210, which is an original three dimensional medical image of a subject, is obtained. The position of each voxel within the aspect image 210 is defined in a three dimensional coordinate system, in which the horizontal direction is the x axis, the front to back direction is the y axis, and the vertical direction is the z axis. The pixel value of each voxel is correlated with the positional coordinates thereof.

Figure 2:
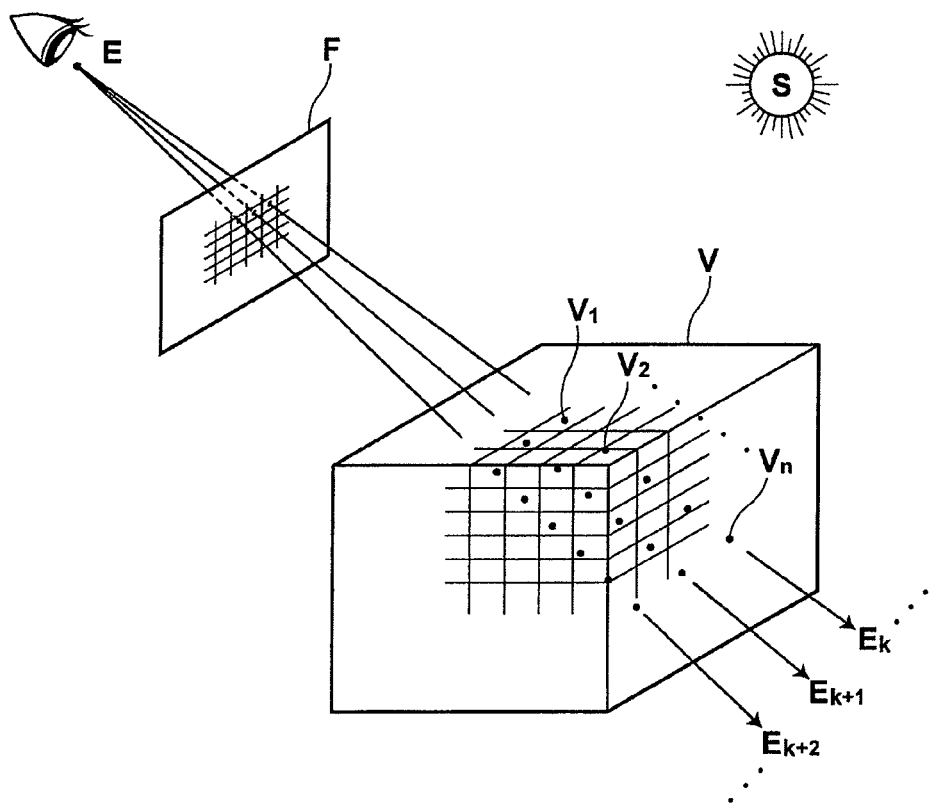

Next, a plurality of search points $v_i$ (i=1, 2, ..., n) are set along a plurality of lines of sight $E_k$ (k=1, 2, ..., L; wherein L is the number of lines of sight) that connect a viewpoint E and a projection plane F, as illustrated in FIG. 2. The search points $v_i$ are points at which an original three dimensional image V is sampled along the plurality of lines of sight $E_k$ at predetermined intervals. Initial values may be employed for the viewpoint E, a light source S, and the projection plane F (size, position, number of pixels thereof, etc.), or an operator may set the values therefor by input via the input means 3 (a keyboard or a mouse, for example).

The brightness value and the degree of opacity of each search point $v_i$ are determined. Thereafter, output pixel values C of projected pixels on the projection plane that each line of sight $E_k$ passes through are determined, based on the brightness value $c(v_i)$ and the degree of opacity $\alpha(v_i)$ of each search point $v_i$ (i=1, 2, ..., n) along each line of sight $E_k$, according to Formula (3) below.

$$C = \sum_{i=1}^{n} c(v_i) \times \alpha(v_i) \prod_{j=1}^{i-1} (1 - \alpha(v_j)) \quad (3)$$

Degrees of opacity are assigned to each pixel value of the aspect image 210 in this manner. Thereby, generation of an image, in which the heart is extracted as the subject, is enabled. The degrees of opacity refer to data which are subject to visualization, and define the aspect of the volume data.

The present invention applies the concept behind this volume rendering method to propose the following method.

At least a functional image 200 and an aspect image 210 are input, and the ray casting technique is executed on the aspect image 210. In the case that there are opaque pixel values which are targets of visualization, the position matching means 50 determines the positions corresponding thereto within the functional image 200. The brightness values of the corresponding positions within the functional image 200 are obtained, and visualization is performed.

Figure 3:
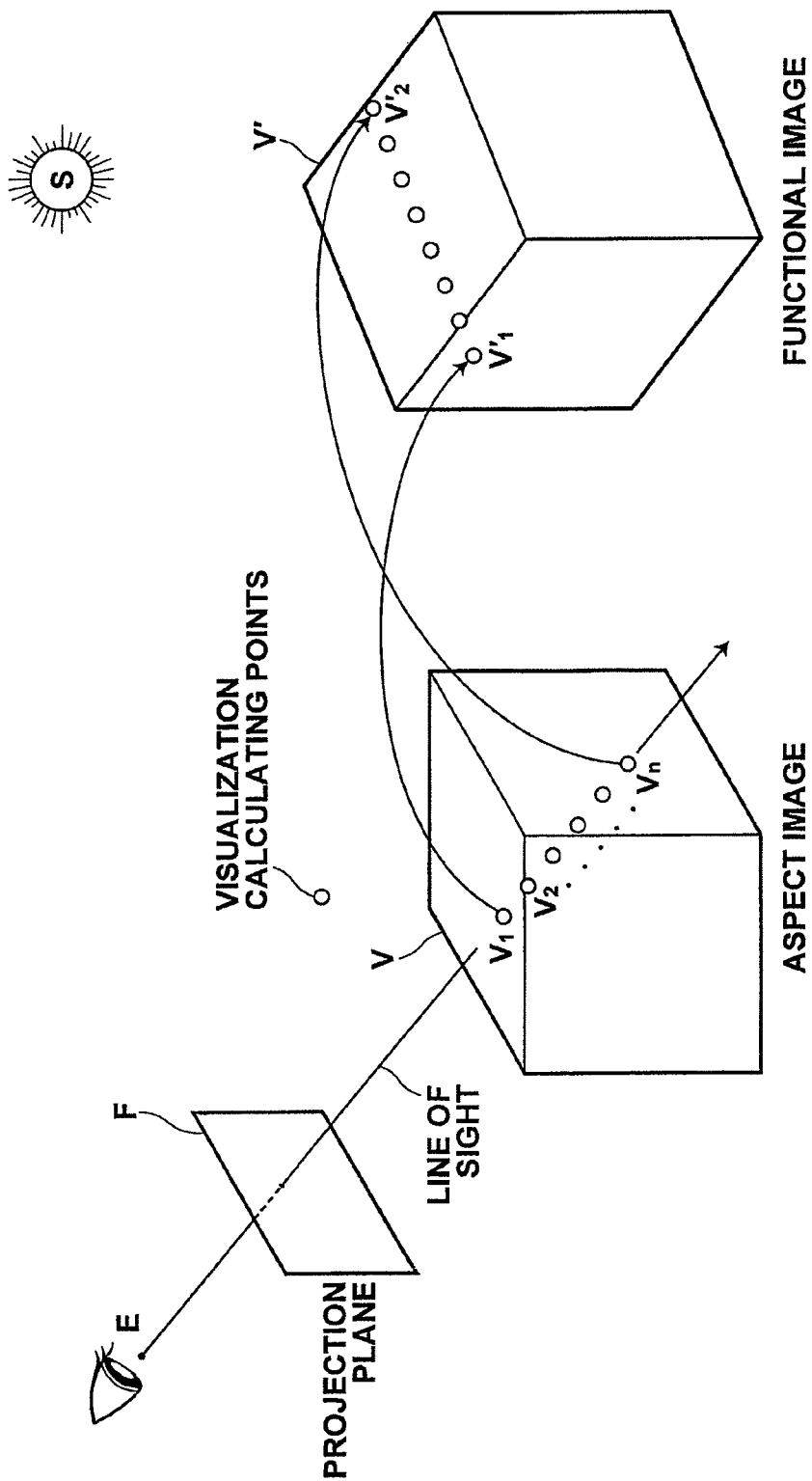

Specifically, search points $v_i$ (i=1, 2, ..., n) related to the aspect image 210, which are sampled at predetermined intervals along a plurality of lines of sight that connect the viewpoint E and each of the projected pixels on the projection plane F, and search points $v'_i$ (i=1, 2, ..., n) related to the mapping functional image 200, corresponding to the search points $v_i$, are set, as illustrated in FIG. 3.

The degree of opacity and the brightness value are obtained for each search point within the aspect image 210. In addition, the degree of opacity and the brightness value of positions within the functional image 200 corresponding to the search points within the aspect image 210 are also obtained. The degrees of opacity obtained from the functional image 200 at each search point are designated as alpha values, and the output pixel values C, which are the aspect image 210 and the functional image 200 blended together, are obtained by performing alpha blending with the brightness values of the aspect image 210 and the brightness values of the functional image 200 according to Formula (4) below.

$$C = \sum_{i=1}^{n} ((1 - \alpha_m(v'_i))c_s(v_i) + \alpha_m(v'_i)c_m(v'_i)) \times \alpha_s(v_i) \prod_{j=1}^{i-1} (1 - \alpha_s(v_j)) \quad (4)$$

Figure 4:
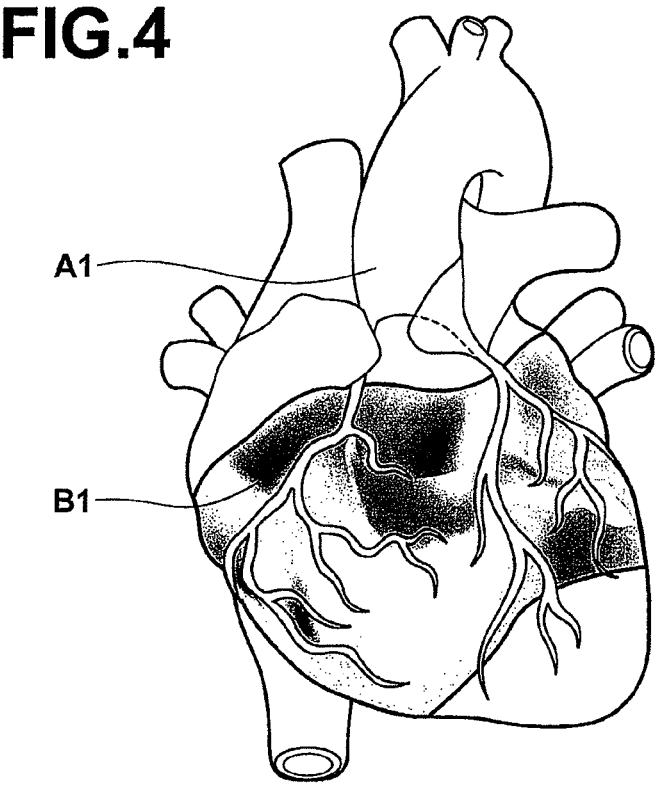

The display means 2 displays a pseudo three dimensional image which is a functional image A1 overlaid on an aspect image B1 as illustrated in FIG. 4, via the image generating means 60. As displayed in FIG. 4, whether the function of the heart is normal and at what portions of the heart the function is normal or abnormal can be observed, based on the positions of blood vessels, through the display means 2.

Data of the functional image 200 regarding positions are mapped onto corresponding positions within the aspect image 210 in this manner. Therefore, visualization of an image in which the data obtained from the functional image is added to the aspect image while maintaining the shape represented therein, is enabled.

Note that it is possible for an operator to change the functional image 200 with another functional image via the input means 3. In this case, a pseudo three dimensional image in which the other functional image 200 is overlaid on the aspect image 210 can be displayed by the display means 2.

Next, the flow of processes which are performed when the three dimensional image processing apparatus 1 is used to display an image, in which an aspect image 210 and a functional image 200 are overlapped, will be described with reference to the flow chart of FIG. 5.

First, images of a subject's heart are obtained by an MRI, and the obtained images are recorded in the first memory means 10 as first voxel data sets 100 (step S100). Further, images of the same subject are obtained by a CT apparatus, and recorded in the second memory means 20 as second voxel data sets 110 (step S101).

The functional image generating means 20 generates a functional image 200 that represents the function of the heart, from the first voxel data sets 100 (step S102).

Next, the aspect image generating means 40 generates an aspect image 210, using the second voxel data sets 110 (step S103).

The position matching means 50 matches the positions within the shapes of the heart represented by the first voxel data sets 100 and the shapes of the heart represented by the second voxel data sets 110. Specifically, for example, the shape of the heart is considered to be a rigid body, and evaluated using correlation coefficients that employ the pixel values of the voxel data sets 100 and 110. Thereby, amounts of displacement when converting from the coordinate system of the functional image to the coordinate system of the aspect image, such as amounts of rotation and amounts of movement, can be determined (step S104).

The degrees of opacity assigned to the functional image 200 that displays the function of the heart, constituted by the first voxel data sets 100 generated by the functional image generating means 20, are designated as alpha values. The image generating means 60 executes a volume rendering process by performing an alpha blending process using the brightness values or the like of the functional image 200 and the aspect image 210 (step S105).

The image generating means 60 generates a pseudo three dimensional image in which the functional image 200 and the aspect image 210 are overlapped, via the aforementioned volume rendering process (step S106).

There are cases in which the first voxel data sets and the second voxel data sets are obtained by a CT apparatus and an MRI apparatus, respectively. There are also cases in which the first voxel data sets and the second voxel data sets are both obtained by either a CT apparatus or an MRI apparatus, but at different slice intervals. In these cases, the aforementioned registration technique can be used to perform position matching. In the case that the image to be processed is a myocardial scintigraphy image, the purposes of imaging are different, and the correlation between an aspect image and a functional image is small. In this case, therefore, favorable position matching may not be possible using the correlations among pixel values. Accordingly, in this case, corresponding characteristic points are selected from each image, and the amount of rotation and the amount of movement for coordinate conversion may be calculated by performing registration among these points.

In the embodiment above, a case in which the coordinate system of the functional image 200 is converted to the coordinate system of the aspect image 210 was described. However, the present invention is not limited to this embodiment, and the coordinate system of the aspect image 210 may be converted to the coordinate system of the functional image 200, or the coordinate systems of both images may be changed, as log as the positions of the heart are matched.

Alternatively, one of the functional image 200 and the aspect image 210 may be generated first. Then, position matching data may be employed to draw the other of the images such that the positions within the image match those of the image which was generated first.

As described above, positions within the functional image and the aspect image are caused to correspond to each other, and volume rendering is executed based on the degree of opacity at each corresponding position of the functional image. Thereby, data of the functional image which is present at positions corresponding to those in the aspect image can be mapped, and a pseudo three dimensional images which is not dependent on the shape of the functional image, but is faithful to the shape of the aspect image, can be generated.

The present invention is based on the volume rendering method with respect to visualization of aspect images. The present invention includes the feature of volume rendering, that data regarding inner structures is maintained and visualized as opaque objects. Therefore, the data of the functional image is mapped not only onto the surface of the object but also onto the interior thereof. Accordingly, mapping is not limited to the surface of the shape of the heart's outer appearance, but mapped data can also be visualized within the interior thereof, by setting a more transparent degree of opacity.

Further, the image data displayed by the display means 2 may be reversibly or irreversibly compressed and output (in the JPEG format, for example). Thereby, medical images, which are large data files, can be compressed, which facilitates data transfer, utilization as presentation materials, and the like.

What is claimed is:

1. An image processing apparatus, comprising:
mapping image generating means, for generating a mapping image M that represents a portion of a subject, by employing a first voxel data set, which is a voxel data set of a three dimensional image that represents the subject with a degree of opacity assigned to each voxel thereof;
aspect image generating means, for generating an aspect image S that represents the aspect of a target which includes at least a portion of the subject from a second voxel data set of the three dimensional image that represents the subject with a degree of opacity assigned to each voxel thereof; and
image generating means, for generating a pseudo three dimensional image, by matching the mapping image M and the aspect image S and executing volume rendering, wherein the image generating means executes volume rendering by:
setting an alpha value based on a degree of opacity $\alpha_m$ of each determined voxel $v_i'$ of the mapping image, for performing alpha blending processing, wherein said determined voxels $v_i'$ of the mapping image are determined as voxels $v_i'$ of the mapping image which correspond to voxels $v_i$ of the aspect image which are to be used in volume rendering, and
obtaining a pseudo three dimensional image having pixel values C by blending the mapping image and the aspect image with formula (4):

$$C = \sum_{i=1}^{n} ((1-\alpha_m(v_i'))c_s(v_i) + \alpha_m(v_i')c_m(v_i')) \times \alpha_s(v_i) \prod_{j=1}^{i-1} (1-\alpha_s(v_j)) \quad (4)$$

wherein
$c_s$ are brightness values, and $\alpha_s$ are degree of opacity for each point $v_i$ of the aspect image to be used in volume rendering, and
$c_m$ are brightness values, and $\alpha_m$ are degree of opacity for each determined voxel $v_i'$ of the mapping image,
wherein said obtaining comprises:
calculating, with respect to said each point to be used for the volume rendering, a blended brightness value with formula (4), by
performing alpha blending processing for each of said determined voxel $v_i'$ of the mapping image, to obtain a calculated blended value, by applying said alpha values to:
the brightness values $c_m$ for each point $v_i'$ of the mapping image to be used in volume rendering, and
the brightness values $c_s$ of the points $v_i$ in the aspect image to be used for the volume rendering, and
executing volume rendering with formula (4) based on the calculated blended value and the degree of opacity $\alpha_s$ assigned to each voxel $v_i$ of the aspect image used in volume rendering.

2. An image processing apparatus as defined in claim 1, wherein:
the image generating means executes volume rendering using a ray casting technique.

3. An image processing apparatus as defined in claim 2, wherein:
the image generating means generates pseudo three dimensional image data, by overlapping the mapping image and the aspect image.

4. An image processing apparatus as defined in claim 2, wherein: the mapping image is a functional image that represents a function of a target tissue system.

5. An image processing apparatus as defined in claim 1, wherein:
the image generating means generates pseudo three dimensional image data, by overlapping the mapping image and the aspect image.

6. An image processing apparatus as defined in claim 1, wherein:
the mapping image is a functional image that represents a function of a target tissue system.

7. The image processing apparatus as defined in claim 1, wherein:
the image generating means calculates brightness values which are the brightness values of the aspect image and the brightness values of the mapping image blended together such that the ratio of the brightness values of the mapping image in the blend becomes higher as the value of the degree of opacity of the mapping image is greater, and generates the pseudo three dimensional image by extracting volume rendering employing the blended brightness values.

8. The image processing apparatus as defined in claim 1, wherein:
the second voxel data set has degrees of opacity assigned to each pixel thereof, and the image generating means executes volume rendering using products of the blended brightness values and the degrees of opacity assigned to each pixel of the second voxel data set, without using the degrees of opacity assigned to the pixels of the first voxel data set.

9. An image processing method, comprising:
a mapping image generating step, for generating a mapping image M that represents a portion of a subject, by employing a first voxel data set, which is a voxel data set of a three dimensional image that represents the subject with a degree of opacity assigned to each voxel thereof;
an aspect image generating step, for generating an aspect image S that represents the aspect of a target which includes at least a portion of the subject from a second voxel data set of the three dimensional image that represents the subject with a degree of opacity assigned to each voxel thereof; and
an image generating step, for generating a pseudo three dimensional image, by matching the mapping image M and the aspect image S and executing volume rendering, the image generating step executes volume rendering by:
setting an alpha value based on a degree of opacity $\alpha_m$ of each determined voxel $v_i'$ of the mapping image, for performing alpha blending processing, wherein said determined voxels $v_i'$ of the mapping image are determined as voxels $v_i'$ of the mapping image which correspond to voxels $v_i$ of the aspect image which are to be used in volume rendering, and
obtaining a pseudo three dimensional image having pixel values C by blending the mapping image and the aspect image with formula (4):

$$C = \sum_{i=1}^{n} ((1 - \alpha_m(v_i'))c_s(v_i) + \alpha_m(v_i')c_m(v_i')) \times \alpha_s(v_i) \prod_{j=1}^{i-1} (1 - \alpha_s(v_j)) \quad (4)$$

wherein
$c_s$ are brightness values, and $\alpha_s$ are degree of opacity for each point $v_i$ of the aspect image to be used in volume rendering, and
$c_m$ are brightness values, and $\alpha_m$ are degree of opacity for each determined voxel $v_i'$ of the mapping image,
said obtaining step comprising:
calculating, with respect to each said point to be used for the volume rendering, a blended brightness value with formula (4), by
performing alpha blending processing for each of said determined voxel $v_i'$ of the mapping image, to obtain a calculated blended value, by applying said alpha values to:
the brightness values $c_m$ for each point $v_i'$ of the mapping image to be used in volume rendering, and
the brightness values $c_s$ the points $v_i$ in the aspect image to be used for the volume rendering, and
executing volume rendering with formula (4) based on the calculated blended value and the degree of opacity $\alpha_s$ to each voxel $v_i$ of the aspect image used in volume rendering.

10. The image processing method as defined in claim 9, wherein:
the image generating step calculates brightness values which are the brightness values of the aspect image and the brightness values of the mapping image blended together such that the ratio of the brightness values of the mapping image in the blend becomes higher as the value of the degree of opacity of the mapping image is greater, and generates the pseudo three dimensional image by extracting volume rendering employing the blended brightness values.

11. The image processing method as defined in claim 9, wherein:
the second voxel data set has degrees of opacity assigned to each pixel thereof, and the image generating step executes volume rendering using products of the blended brightness values and the degrees of opacity assigned to each pixel of the second voxel data set, without using the degrees of opacity assigned to the pixels of the first voxel data set.

12. A non-transitory computer readable medium having recorded therein a program that causes a computer to function as:
mapping image generating means, for generating a mapping image M that represents a portion of a subject, by employing a first voxel data set, which is a voxel data set of a three dimensional image that represents the subject with a degree of opacity assigned to each voxel thereof;
aspect image generating means, for generating an aspect image S that represents the aspect of a target which includes at least a portion of the subject from a second voxel data set of the three dimensional image that represents the subject with a degree of opacity assigned to each voxel thereof; and image generating means, for generating a pseudo three dimensional image, by matching the mapping image M and the aspect image S and executing volume rendering, the image generating means executes volume rendering by:
  setting an alpha value based on a degree of opacity $\alpha_m$ of each determined voxel $v_i'$ of the mapping image, for performing alpha blending processing, wherein said determined voxels $v_i'$ of the mapping image are determined as voxels $v_i'$ of the mapping image which correspond to voxels $v_i$ of the aspect image which are to be used in volume rendering, and
  obtaining a pseudo three dimensional image having pixel values C by blending the mapping image and the aspect image with formula (4):

$$C = \sum_{i=1}^{n} ((1 - \alpha_m(v_i'))c_s(v_i) + \alpha_m(v_i')c_m(v_i')) \times \alpha_s(v_i) \prod_{j=1}^{i-1} (1 - \alpha_s(v_j)) \quad (4)$$

wherein
  $c_s$ are brightness values, and $\alpha_s$ are degree of opacity for each point $v_i$ of the aspect image to be used in volume rendering, and
  $c_m$ are brightness values, and $\alpha_m$ are degree of opacity for each determined voxel $v_i'$ of the mapping image,
wherein said obtaining comprises:
calculating, with respect to said each point to be used for the volume rendering, a blended brightness value with formula (4), by
  performing alpha blending processing for each of said determined voxel $v_i'$ of the mapping image, to obtain a calculated blended value, by applying said alpha values to:
    the brightness values $c_m$ for each point $v_i'$ of the mapping image to be used in volume rendering, and
    the brightness values $c_s$ of the points $v_i$ in the aspect image to be used for the volume rendering, and
  executing volume rendering with formula (4) based on the calculated blended value and the degree of opacity $\alpha_s$ to each voxel $v_i$ of the aspect image used in volume rendering.

13. The non-transitory computer readable medium as defined in claim 12, wherein:
  the image generating means calculates brightness values which are the brightness values of the aspect image and the brightness values of the mapping image blended together such that the ratio of the brightness values of the mapping image in the blend becomes higher as the value of the degree of opacity of the mapping image is greater, and generates the pseudo three dimensional image by extracting volume rendering employing the blended brightness values.

14. The non-transitory computer readable medium as defined in claim 12, wherein:
  the second voxel data set has degrees of opacity assigned to each pixel thereof, and the image generating means executes volume rendering using products of the blended brightness values and the degrees of opacity assigned to each pixel of the second voxel data set, without using the degrees of opacity assigned to the pixels of the first voxel data set.

* * * * *